United States Patent [19]

Fox

[11] Patent Number: 4,887,965
[45] Date of Patent: Dec. 19, 1989

[54] ADJUSTABLE MOUTH PROP

[76] Inventor: Henry L. Fox, 2265 Compass Point La., Reston, Va. 22901

[21] Appl. No.: 228,359

[22] Filed: Aug. 2, 1988

[51] Int. Cl.⁴ ............................................. A61C 3/00
[52] U.S. Cl. ................................................. 433/140
[58] Field of Search ..................... 433/140, 93; 128/12

[56] References Cited

U.S. PATENT DOCUMENTS

| | | | |
|---|---|---|---|
| Re. 20,389 | 6/1937 | Pickett | 128/12 |
| 791,859 | 6/1905 | Barnes | 433/149 |
| 856,852 | 6/1907 | Magoon | 249/184 |
| 1,229,595 | 6/1917 | Du Brul | 433/136 |
| 1,498,219 | 6/1924 | Williams . | |
| 2,019,060 | 10/1935 | Thibert . | |
| 2,023,288 | 12/1935 | Pickett | 128/12 |
| 2,061,936 | 11/1936 | Engelfried | 128/12 |
| 2,103,115 | 12/1937 | Mizzy et al. | 215/260 |
| 2,220,674 | 11/1940 | Bloomheart | 128/12 |
| 2,505,056 | 4/1950 | Messine | 128/12 |
| 2,570,459 | 10/1951 | Kreider | 433/140 |
| 2,587,245 | 2/1952 | Terre . | |
| 2,823,455 | 2/1958 | Sprague . | |
| 3,217,708 | 11/1965 | Roberts | 128/861 |
| 3,483,619 | 12/1969 | Smith | 19/230 |
| 3,722,101 | 3/1973 | Via, Jr. . | |
| 4,056,855 | 11/1977 | Kelman | 24/129 B |
| 4,179,815 | 12/1979 | Hoffman | 433/140 |
| 4,573,919 | 3/1986 | Sinkora | 433/140 |
| 4,632,093 | 12/1986 | Giorni | 128/12 |

Primary Examiner—R. Peshock
Attorney, Agent, or Firm—Pollock Vande Sande & Priddy

[57] ABSTRACT

The present invention provides a unitary, adjustable mouth prop having jaw engaging plates connected by a spring. The plates hold a resilient molding material to comfortably and securely contact a patient's teeth. The plates are further connected by an adjusting mechanism which is used to adjust and maintain a controlled occlusal opening. The adjusting mechanism is made of a screw extending from each plate and an internally threaded sleeve connecting the two screws. The sleeve is threaded to either draw together or separate the screws and their attached jaw engaging plates, thereby closing or opening the occlusal opening. This sleeve and screw adjusting mechanism allows for easy and gradual adjustment of the size of the occlusal opening, without disruption of the dental procedure or discomfort to the patient.

14 Claims, 2 Drawing Sheets

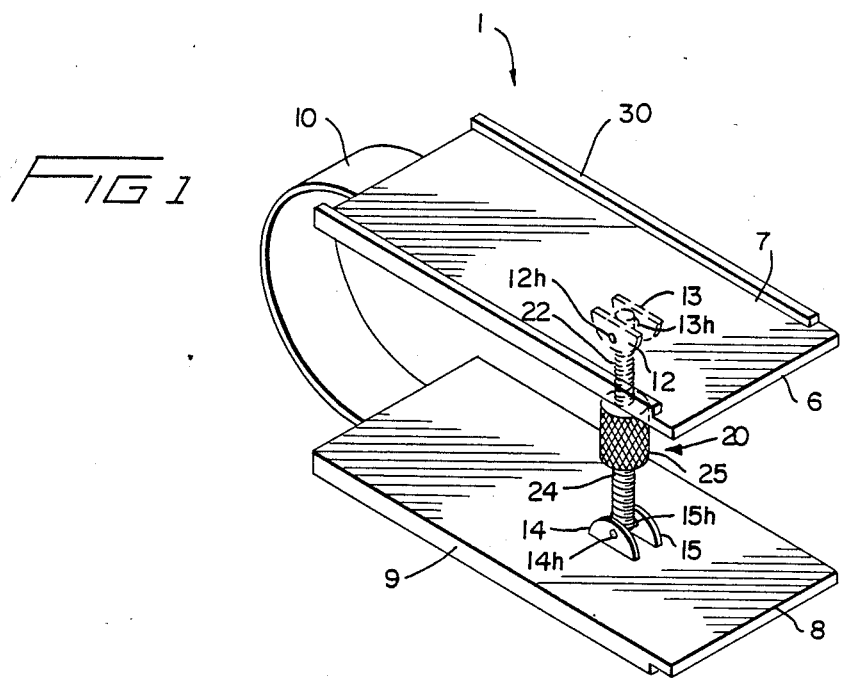
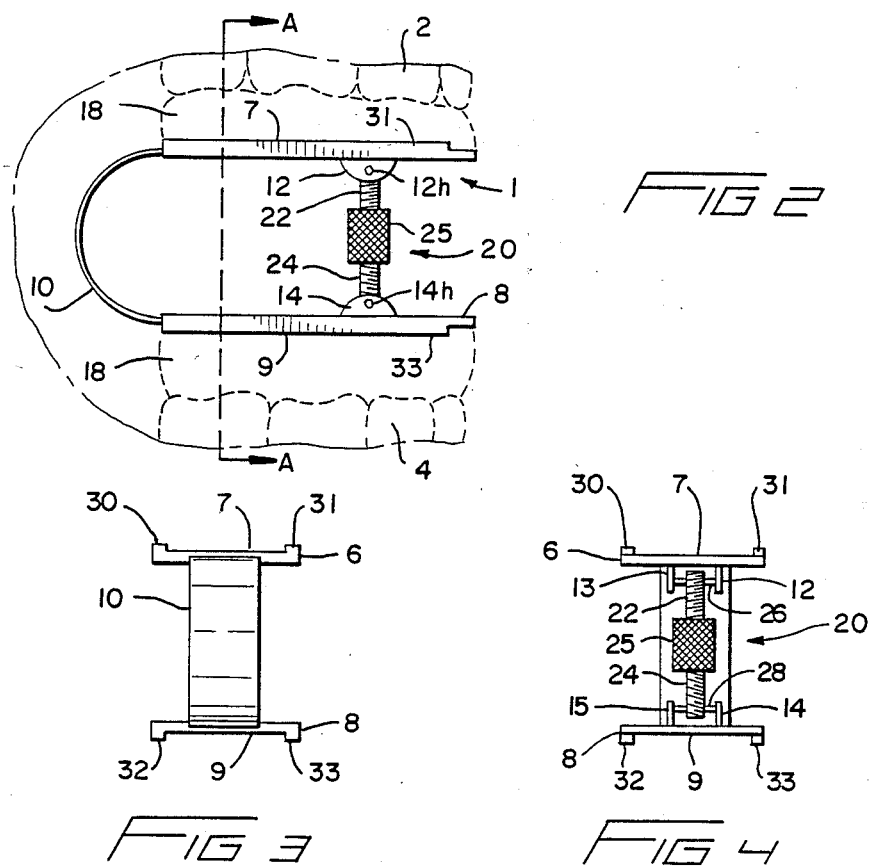

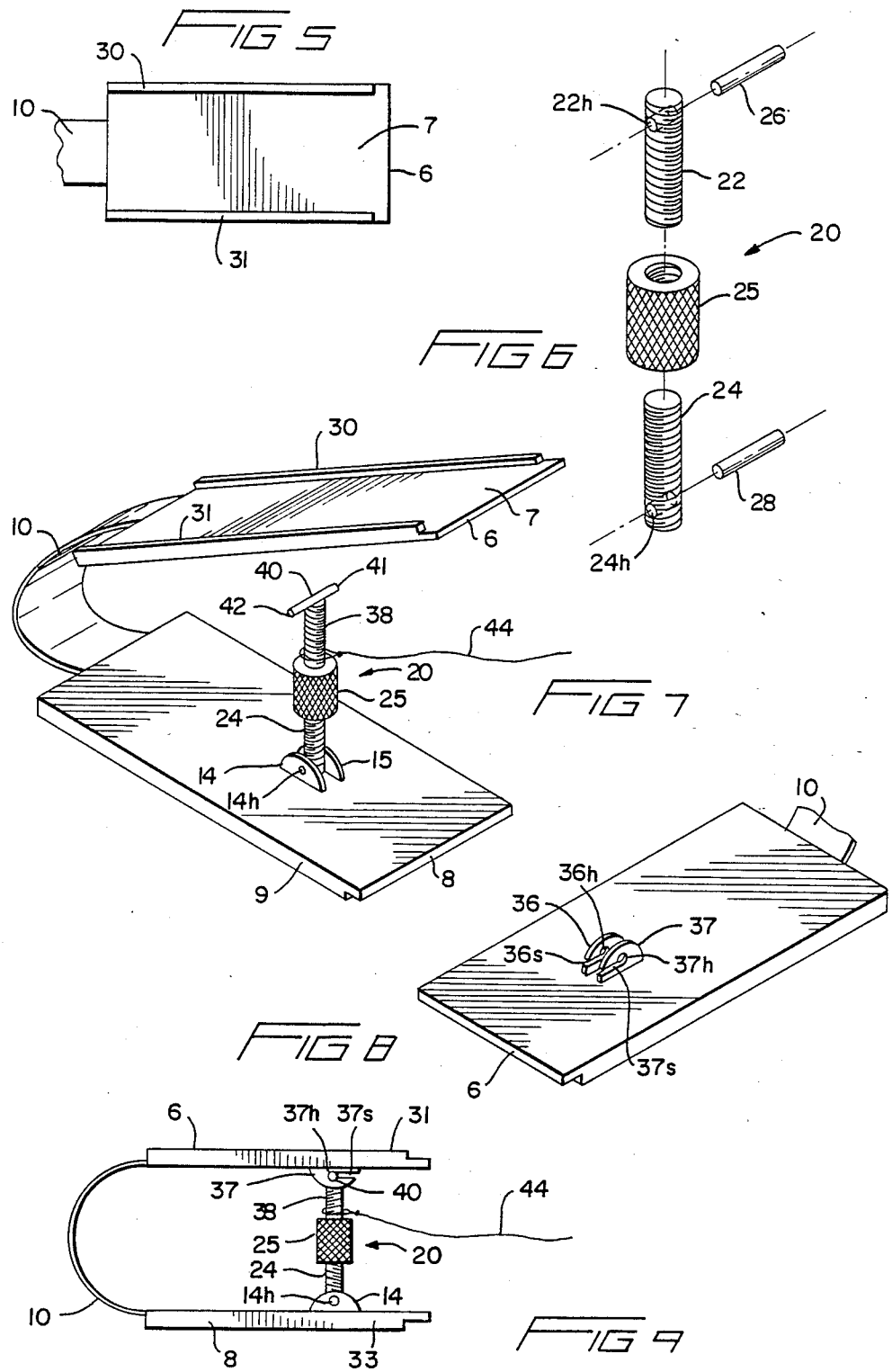

ADJUSTABLE MOUTH PROP

FIELD OF THE INVENTION

This invention relates to mouth props, and specifically to a unitary, adjustable mouth prop that provides a controlled occlusal opening for a patient and a comfortable support onto which the patient may rest his teeth. Further, the mouth prop to which this invention relates tends to remain stable within the patient's mouth and provides the dentist, and his assistant, maximum access to the inside of the patient's mouth.

BACKGROUND OF THE INVENTION

During dental procedures, it is often difficult for the patient to hold his mouth open for extended lengths of time due to muscle fatigue. Mouth props, or bite blocks, are often lodged between a patient's upper and lower teeth to hold the mouth open. However, a desirable mouth prop must also be comfortable for the patient and usable with different patients, or with a single patient under varied conditions.

Further, to enable the dentist to maintain the patient's mouth open to a degree most comfortable for the patient and to provide maximum access to the inside of the patient's mouth, a mouth prop ought to be adjustable.

Several adjustable mouth props have been designed. In U.S. Pat. No. 2,023,288 and RE No. 20,389 to Pickett, a mouth prop made adjustable by a wedge having beveled notches was disclosed. The wedge is forced between opposed jaw engaging members to open the patient's mouth. The beveled notches engage a lug on one of the jaw engaging members to secure the wedge in place. However, the use of notches and a lug in the Pickett mouth prop provides for only incremental adjustment. Also, the beveled notches of the Pickett mouth prop provide for smooth adjustment only when the wedge is inserted further into the mouth. This means that, were the patient's mouth to be closed only slightly, the wedge has to be completely retracted. The fact that the patient first has to open his mouth in order for the wedge to be removed and repositioned means that the dental procedure has to be interrupted, thereby prolonging patient discomfort.

Further, the Pickett mouth prop comprises two pieces. This poses the risk that one of the pieces may be lost by the dentist or swallowed by the patient. Furthermore, the wedge and the jaw engaging members form a barrier on one side of the patient's mouth which obstructs the view of the working area of the mouth for an assistant, were assistance required during the dental procedure.

U.S. Pat. No. 2,103,115 to Mizzy, et al. discloses a dental jack that provides for continuous adjustment by means of a screw and a threaded sleeve. Although the Mizzy mouth prop allegedly provides an unobstructed view of the working area of the patient's mouth, it is unstable when used solely as a mouth prop, due to its pin-shaped contact with the teeth.

U.S. Pat. Nos. 856,352 to Magoon and 2,019,060 to Thibert both teach mouth props having a spring surrounding a telescopic shaft connecting two jaw engaging members to hold open a patient's mouth. The telescopic shaft of both Magoon and Thibert mouth props have an outer and an inner shaft member. In order to adjust the Magoon mouth prop, the outer shaft member is tilted to rest on the notches of the inner shaft member. The Thibert mouth prop relies on friction between the tilted outer shaft member and the inner shaft member to adjust and maintain the occlusal opening. These mouth props are designed to be used with a patient who is under anesthesia—when the jaw muscles of the patient are relaxed and do not need strong support. Therefore, these mouth props are not sturdy enough to support fatigued and possibly tense muscles of a conscious patient.

SUMMARY OF THE INVENTION

The present invention overcomes the disadvantages of the above-mentioned existing mouth props by providing a sturdy, unitary mouth prop that fits securely into a patient's mouth and can quickly provide for a non-incremental occlusal opening.

When assistance in the procedure is required, the present invention further provides advantageously a substantially unobstructed view of the working area of the mouth, by creating a minimal barrier between the patient's upper and lower teeth.

Accordingly, the present invention includes jaw engaging plates that are connected by a spring. The plates hold resilient molding material which comfortably and securely contact the teeth of a patient. The jaw engaging plates are also connected by an adjustment mechanism which may be comprised of a screw fixedly extending from each plate and an internally threaded sleeve connecting the two screws. The size of the occlusal opening is adjusted by turning the sleeve, clockwise or counterclockwise, so as to thread the screws and, thus, move the attached jaw-engaging plates either together or apart.

In a second embodiment of the invention, the mouth prop is collapsible for immediate removal from the patient's mouth, by making the adjustment mechanism releasably connected to one plate.

Since the adjustment mechanism is constructed of screws and a sleeve, the present invention mouth prop eliminates the disadvantages of the notched adjustment of the Pickett and Magoon mouth props by being able to be adjustable so as to maintain an occlusal opening that is precisely tailored to the patient and to the to be conducted procedure.

Also, since adjusting the present invention mouth prop involves merely turning a sleeve, the size of the occlusal opening can be opened or closed quickly and continuously without having to remove the device or any portion thereof, disrupting the dental procedure, or increasing discomfort to the patient.

Further, the screw and sleeve adjustment mechanism of the present invention mouth prop appears to be smaller than the wedge used in the prior art, for example in the Pickett mouth prop. Therefore, the present invention mouth prop provides a substantially less obstructed view of the working area of the patient's mouth than that provided in the prior art.

The present invention also overcomes the inability of the prior art mouth props—such as those of Magoon and Thibert to provide a sturdy bite rest for a patient's fatigued muscles—by providing two separate sources of support for the patient's bite.

Finally, unlike the two piece Pickett mouth prop, the present invention mouth prop involves no loose or separable pieces during use. Consequently, the likelihood that the patient will swallow any portion of the device is eliminated.

BRIEF DESCRIPTION OF THE DRAWINGS

The above-mentioned objectives and advantages of the present invention will become more apparent and the invention itself will be better understood when viewed in conjunction with the following figures, wherein:

FIG. 1 is a perspective view of a mouth prop according to the present invention;

FIG. 2 is a side view of the FIG. 1 mouth prop, the resilient molding material being shown in phantom;

FIG. 3 is a back view of the mouth prior of FIG. 1;

FIG. 4 is a cross-sectional view of the mouth prop of FIG. 2, taken along line A—A;

FIG. 5 is a plan view of the mouth prop of FIG. 1, particularly showing the location of the flanges;

FIG. 6 is an exploded, isolated view of the adjustment mechanism of the mouth prop of FIG. 1;

FIG. 7 is a perspective view of a second embodiment of the mouth prop according to the present invention;

FIG. 8 is an isolated, perspective view of the underside of member 6 according to the embodiment of FIG. 7, showing in particular the construction of shoulders 36 and 37 and slots 36s and 37s; and FIG. 9 is a side view of the FIG. 7 embodiment, showing the adjustment mechanism connected to member 6.

DESCRIPTION OF THE PREFERRED EMBODIMENTS

To be used, as envisioned, by dentists and oral surgeons, the present invention mouth prop 1, illustrated perspectively in FIG. 1, is to be inserted into one side of a patient's mouth between opposing occlusal surfaces 2 and 4, as shown in FIG. 2.

Mouth prop 1 is made of two opposing members 6 and 8 having respective jaw engaging surfaces 7 and 9. Members 6 and 8 are connected at corresponding ends thereof by a leaf spring 10. However, it should be appreciated that other connecting means, such as a coiled spring, may also be used.

Member 6 has two shoulders 12 and 13, shoulder 12 having pinhole 12h and shoulder 13 having pinhole 13h. Similarly, member 8 has two shoulders 14 and 15, shoulder 14 having pinhole 14h and shoulder 15 having pinhole 15h. The purpose of the shoulders and pinholes will be described later.

Referring to FIG. 2, surfaces 7 and 9 on members 6 and 8, respectively, are configured to hold a resilient molding material 18. Molding material 18 is used to intimately contact the upper teeth 2 and lower teeth 4 of the patient, affording a safe and comfortable bite rest therefor by conforming to the contours of the teeth 2 and 4 and to the respective jaw engaging surfaces 7 and 9. Molding material 18 further stabilizes mouth prop 1 within the patient's mouth and prevents the mouth prop from dislodging. Molding material 18 is preferably a vinyl polysiloxan, such as Perform, manufactured by The Columbus Dental Company; or Omnisil, manufactured by The Coe Company. It should be appreciated that the molding material is not limited to the above-mentioned materials, but may also be Rubber Base Material manufactured by, among others, The Coe Company, or wax.

Jaw engaging surface 7 may have flanges 30 and 31 arranged thereon or integral therewith to hold molding material 18 more securely. Jaw engaging surface 9 may similarly have flanges 32 and 33 arranged thereon. Any convenient configuration of flanges is contemplated by the present invention, including a single flange around the respective perimeters of surfaces 7 and 9, or no flanges at all.

Referring to FIGS. 2, 4 and 6, the size of the occlusal opening formed by mouth prop 1 is determined and changed by an adjusting means 20. Adjusting means 20 is connected to member 6 at shoulders 12 and 13, and connected to member 8 at shoulders 14 and 15 in a manner hereinafter described.

Referring specifically to FIG. 6, adjusting means 20 is formed by screws 22 and 24. Screw 22 has a pinhole 22h at one end thereof and screw 24, similarly, has a pinhole 24h at a corresponding one end thereof. Internally threaded adjustment sleeve 25 connects screws 22 and 24 at their respective other ends. Screws 22 and 24 are positioned with respect to adjustment sleeve 25 so that the rotational orientations of the screws are reversed. In this manner, turning the adjustment sleeve will cause both screws 22 and 24 to either exit or enter the sleeve concurrently, thereby expanding or contracting the distance between members 6 and 8. Screws 22 and 24 are connected to members 6 and 8, respectively, in the following manner.

Referring to FIG. 4, screw 22 is positioned between shoulders 12 and 13 so that pinhole 22h, of screw 22 and pinholes 12h and 13h of shoulders 12 and 13, respectively, are aligned. Pin 26 is inserted through pinholes 12h, 22h and 13h to give screw 22 and member 6 a pivotal relationship. Similarly, screw 24 is positioned between shoulders 14 and 15 so that respective pinholes 24h, 14h and 15h are aligned. Pin 28 is inserted through pinholes 14h, 24h and 15h to provide a pivotal relationship between screw 24 and member 8. The respective pivotal relationships between screw 22 and member 6 and between screw 24 and member 8 allow the screws to align for connection adjustment by adjustment sleeve 25, regardless of the spacing between members 6 and 8. As can readily be seen, since the members 6 and 8 each has one of its ends correspondingly connected to leaf spring 10, if the members are not secured to adjusting means 20, per FIG. 7, the angular orientation between members 6 and 8, at their respective ends which are not connected to leaf spring 10, would change as members 6 and 8 diverge. Therefore, by virtue of the aforementioned pivotal relationships, members 6 and 8 would angularly diverge at their respective ends not connected to leaf spring 10 as they separate to thereby effectively force molding material 18 to firmly conform to the mouth of the patient.

In use, mouth prop 1 is assembled as shown in FIG. 1. A slab of molding material 18 is set on respective jaw engaging surfaces 7 and 9 of members 6 and 8. The mouth prop is then inserted into the patient's mouth, with connecting spring 10 being positioned toward the back of the mouth, as shown in FIG. 2. The patient is instructed to bite down onto the mouth prop in order to effect a tailored impression of the teeth onto molding material 18, and thus a stabilized fitting between the mouth prop and the teeth. Adjustment sleeve 25 may be turned without interruption to separate members 6 and 8, thereby opening the patient's mouth, i.e. members 6 and 8 are spatially arranged to fit the mouth opening of the patient.

A patient may comfortably rest his teeth on the present invention mouth prop when it is inserted as described. The size of the occlusal opening may be increased or decreased by merely turning the adjustment sleeve 25. Thus, any size mouth opening can be accommodated by the present invention mouth prop. Since the adjusting means creates only a minimal barrier, a virtually unobstructed view of the working area of the patient's mouth is thus provided—this is desirable in the event that more than one person needs to participate in the dental procedure.

When the procedure is completed, adjustment sleeve 25 may be rotated to close the distance between members 6 and 8. The patient can then comfortably disengage his teeth from the molding material and the mouth prop can be removed. The molding material is removed from members 6 and 8 and discarded. The mouth prop may then be sterilized and reused with other patients. Alternatively, the mouth prop may be constructed of a disposable material, such as plastic, so that it is discarded after use.

The present invention also contemplates a safety feature in a second embodiment. With reference to FIGS. 7-9. One end of adjusting means 20 may be releasably connected to either member 6 or member 8. Referring to member 6, understanding that reference may also be made to member 8, shoulders 36 and 37 have corresponding slots 36s and 37s connected to respective pinholes 36h and 37h. Pin 40 is fixedly connected to screw 38 so that pin ends 41 and 42 extend from screw 38. To connect adjusting means 20 to member 6, ends 41 and 42 of pin 40 are snapped into pinholes 36h and 37h through slots 36s and 37s, respectively. See FIG. 9. Screw 38 retains a pivotal relationship with member 6 for alignment and connection with screw 24.

When mouth prop 1 must be removed from the patient's mouth immediately, as in the case of an emergency, pin 40 is snapped out of engagement with shoulders 36 and 37, thereby causing the entire adjusting means to collapse away from member 6, by virtue of the pivotal relationship between screw 24 and member 8. The safety of this collapsible feature is enhanced by the fact that upon the disengagement of pin 40 from member 6, the entire adjusting means 20 remains connected to the mouth prop via screw 24 and member 8. Therefore, there are no loose parts for the patient to swallow accidentally.

A further safety feature contemplated for this invention involves attaching a string 44 to mouth prop 1, as shown in FIGS. 7 and 9. String 44 is tied to adjusting means 20, preferably at screw 38. Thus, a dentist needs only to pull on string 44 to disengage screw 38 from shoulders 36 and 37, thereby easily disconnecting adjusting means 20 from member 6. This feature is particularly useful when the dentist cannot reach into the patient's mouth or locate the adjusting means, as when the mouth prop becomes dislodged and positioned erroneously within the patient's mouth.

Any variations or modifications of the present invention envisioned by one of ordinary skill in the art are contemplated to be within the scope of this invention.

I claim:

1. A mouth prop comprising:
   a first member;
   a second member opposed to said first member, said first and second members having respective jaw engaging surfaces for holding a resilient molding material to intimately contact opposing occlusal surfaces of a patient;
   means for flexibly connecting said first and second members;
   means for adjusting the distance between said opposed members to spatially arrange without interruption said occlusal surfaces to fit any mouth opening, said adjusting means having a first and second extension movably connected respectively to said first and second members.

2. A mouth prop according to claim 1 wherein said flexible connecting means is U-shaped.

3. A mouth prop according to claim 1 wherein said flexible connecting means is a U-shaped leaf spring.

4. A mouth prop according to claim 1, further comprising flanges arranged along at least the length of said jaw engaging surfaces of said first and second members.

5. A mouth prop according to claim 1, wherein said adjusting means further comprises turning means adapted to connect said first and second extensions for changing without interruption said distance between said first and second members.

6. A mouth prop according to claim 5, wherein said turning means comprises a sleeve for threadedly connecting said first and second extensions.

7. A mouth prop according to claim 1 wherein said first and second extensions are screws.

8. A mouth prop comprising:
   a first member;
   a second member opposed to said first member, said first and second members having respective jaw engaging surfaces for holding a resilient molding material to intimately contact opposing occlusal surfaces of a patient;
   means for flexibly connecting said first and second members;
   means for adjusting without interruption the distance between said opposed members to spatially arrange said occlusal surfaces to fit any mouth opening, said adjusting means having a first and a second extension movably connected respectively to said first and second members, one of said extensions adaptable to be quickly disconnected from its corresponding member so that said adjusting means can collapse away from one of said members and the mouth prop can immediately be withdrawn from the mouth of the patient.

9. A mouth prop according to claim 8, wherein said flexible connecting means is U-shaped.

10. A mouth prop according to claim 8, wherein said flexible connecting means is a U-shaped leaf spring.

11. A mouth prop according to claim 8, further comprising flanges arranged along at least the length of said jaw engaging surfaces of said first and second members.

12. A mouth prop according to claim 8, wherein said adjusting means further comprising a turning means adapted to connect said fixed and releasable extensions for changing without interruption said distance between said first and second members.

13. A mouth prop according to claim 12 wherein said turning means comprises a sleeve for threadedly connecting said fixed and releasable extensions.

14. A mouth prop according to claim 8 wherein said fixed and releasable extensions are screws.

* * * * *